(12) United States Patent
Roddenbery et al.

(10) Patent No.: US 7,399,324 B2
(45) Date of Patent: Jul. 15, 2008

(54) ACTIVE AGENT DELIVERY DEVICE

(75) Inventors: Ed Roddenbery, Columbus, GA (US); Robert Stover, Thomasville, GA (US); Charles D. Black, Jr., Cleveland, GA (US); Robert M. Fuller, Helen, GA (US)

(73) Assignee: Camovision of Georgia, LLC, Columbus, GA (US)

( * ) Notice: Subject to any disclaimer, the term of this patent is extended or adjusted under 35 U.S.C. 154(b) by 920 days.

(21) Appl. No.: 10/765,906

(22) Filed: Jan. 29, 2004

(65) Prior Publication Data

US 2005/0169952 A1    Aug. 4, 2005

(51) Int. Cl.
*C10L 5/36* (2006.01)
*C10L 11/00* (2006.01)

(52) U.S. Cl. .............. 44/530; 44/532; 44/533; 44/540; 44/542; 44/543; 44/550

(58) Field of Classification Search ............ 44/530, 44/532, 533, 540, 542, 543, 550
See application file for complete search history.

(56) References Cited

U.S. PATENT DOCUMENTS

| | | | |
|---|---|---|---|
| 418,316 A | 12/1889 | Fire-Kindler | |
| 2,854,321 A | 9/1958 | Stanton | |
| 3,540,865 A | 11/1970 | Pape et al. | |
| 3,613,658 A | 10/1971 | Kwoles et al. | |
| 4,020,156 A | 4/1977 | Murray et al. | |
| 4,144,121 A | 3/1979 | Otouma et al. | |
| 4,162,924 A | 7/1979 | Kubo et al. | |
| 4,298,386 A | 11/1981 | Kubo et al. | |
| 4,334,931 A | 6/1982 | Asaumi et al. | |
| 4,647,499 A | 3/1987 | Takahashi et al. | |
| 4,788,164 A | 11/1988 | Che et al. | |
| 4,840,672 A | 6/1989 | Baes | |
| 5,032,549 A | 7/1991 | Lang et al. | |
| 5,035,886 A | 7/1991 | Chakrabarti et al. | |
| 5,573,984 A | 11/1996 | Breitenbucher et al. | |
| 5,858,384 A | 1/1999 | Levy | |
| 5,990,057 A | 11/1999 | Sharp | |

OTHER PUBLICATIONS

Xonotlite. [online]. [retrieved on Oct. 30, 2003]. Retrieved from the Internet: <URL: http://euromin.w3sites.net/mineraux/XONOTLITE.html>.

(Continued)

*Primary Examiner*—Cephia D Toomer
(74) *Attorney, Agent, or Firm*—Browdy and Neimark

(57) ABSTRACT

A sustained release composite is made from a three-dimensional piece of calcium silicate having a xontolite structure and in which are fibers of textile glass and borosilicate glass, and an active agent. The active agent can be a fire starting material, a fragrance, or a masking fragrance.

8 Claims, 2 Drawing Sheets

Calcium silicate block laying flat

A

Calcium silicate block on its side

B

Calcium silicate block standing on end

C

U.S. PATENT DOCUMENTS

| | | |
|---|---|---|
| 6,093,224 A | 7/2000 | Jones |
| 6,136,053 A | 10/2000 | Sullivan |
| 6,199,546 B1 | 3/2001 | Freemon |
| 6,245,733 B1 | 6/2001 | Mosbaugh |
| 6,379,405 B1 | 4/2002 | Reiger et al. |
| 6,508,849 B1 | 1/2003 | Comas |
| 6,692,678 B2 | 2/2004 | Krowl et al. |
| 2005/0037300 A1 | 2/2005 | Snyman |
| 2005/0076898 A1* | 4/2005 | Noble .................. 126/25 B |

OTHER PUBLICATIONS

Xonotlite. [online]. Mineral data Pronunciation Guide. [retrieved on Oct. 30, 2003] Retrieved from the Internet. <URL: http://webmineral.com/data/Xonolite.shtml>.

Mineral description: Xonotlite. [online]. [retrieved on Oct. 30, 2003]. Retrieved from the internet: <URL: http://www.geology.neab.net/minerals/xonotlit.htm>.

Easyflame Promotional Material, www.easyflame.com [online]. [retrieved on Feb. 26, 2004].

* cited by examiner

Calcium silicate block laying flat

A

Calcium silicate block on its side

B

Calcium silicate block standing on end

C

ACTIVE AGENT DELIVERY DEVICE

FIELD OF THE INVENTION

The present invention relates to an active agent delivery device based on calcium silicate that has superior properties to conventional calcium silicate structures.

BACKGROUND OF THE INVENTION

Active agent delivery devices are used to release active agent over a prolonged period of time, or, when the active agent is a fire starting fluid, over a period of time sufficient to ignite combustible material. Many different types of absorbents have been disclosed for slow release of active ingredients such as fragrances or insect repellents.

Levy, in U.S. Pat. No. 5,858,384, discloses silicates that can be used in blocks to trap insecticides for slow release of the insecticides into a body of water. While many different types of porous carriers can be used for this purpose, the preferred materials are silicates which have a surface area of from about 50 to 450 m$^2$/g, an average agglomerate size of from about 3.5 to about 100 microns or an average particle size of from about 12 to 39 nanometers, a tapped density of from about 50 to about 240 g/l, a pH of from about 3.6 to about 9, and a DHP adsorption of about 160 to 335 g/100 g.

Murray et al., in U.S. Pat. No. 4,020,156, disclose fragrance releasing beads comprising a water-soluble particulate carrier coated with a finely divided inorganic matrix containing the fragrance. This matrix may be calcium silicate.

Breitenbucher et al., in U.S. Pat. No. 5,573,984, disclose porous glass bodies for storing volatile substances so as to permit a regulated evolution of the substances.

Mosbaugh, in U.S. Pat. No. 6,245,733, teaches an agglomeration of fused microspheres that can be used to absorb oil or alcohol-based liquids. This can be used as a long term fragrance delivery for slow release of fragrance.

Lang et al., in U.S. Pat. No. 5,032,549, disclose using calcium silicate granules in animal litter and bedding. The calcium silicate is said to have a microporous structure, which as a result of capillary action, is able to absorb oleophilic and hydrophilic liquids as well as gases.

Che et al., in U.S. Pat. No. 4,788,164, disclose sustained release composition consisting of an inorganic oxide glass monolith and a microporous volume that contains a volatile organic component and a nonvolatile organic component. The volatile organic component can be a fragrance, an insect repellant, or a fish attractant.

Chakrabarti et al., in U.S. Pat. No. 5,035,886, discloses active agent delivery devices comprising a microporous material of a matrix of an ultrahigh molecular weight polyolefin, a large amount of filler, at least 50% of which is siliceous, and a releasable active agent.

SUMMARY OF THE INVENTION

It is an object of the present invention to overcome the aforesaid deficiencies in the prior art.

It is another object of the present invention to provide a delivery device for active agents.

It is still another object of the present invention to provide a device that can be used to ignite wood.

It is another object of the present invention to provide a device that can be used to ignite charcoal.

It is still another object of the present invention to provide a device that can be used to release a fragrance.

It is yet another object of the present invention to provide a device that can be used to release scents to camouflage human scent.

According to the present invention, shaped calcium silicate having a structure and composition as described below is used as an absorbent for active agents as well as an absorbent for liquid fire starting materials. The shaped bodies of calcium silicate are prepared by mixing high purity sand and high purity lime in water to form a slurry, and heating the slurry under pressure to form calcium silicate crystals. The calcium silicate crystals are then mixed with about 0.5% wood pulp fibers, from about 0.5% to about 1% textile grade glass fibers and about 1% bentonite clay, pressed into a final shape, and dried. The calcium silicate is in the form of xonotlite crystals.

Xonotlite is a calcium silicate monohydrate ($C_3S_5H$), a natural mineral that is readily synthesized at 150°-350° C. under saturated steam pressure. The empirical formula for xonotlite is $Ca_6Si_6O_{17}(OH)_2$.

A particularly useful calcium silicate material is produced by Industrial Insulation Group LLC as Super FiretempL®. This product is white, essentially dust-free, and contains an extremely low amount of water of hydration. This material consists of a xonotlite crystal structure containing about 0.5% pulp wood fibers, about 0.5-1% textile grade glass fibers, and about 1% by weight of bentonite clay.

The present invention provides blocks in any desired shape or size of this material which are then impregnated with an active agent for subsequent slow release of the active agent. In addition to slow release of the active agent, the blocks of the present invention can be impregnated with ignition fluid and the impregnated block used as a fire starter. Once a match is applied to the impregnated block, the ignition fluid is slowly released to the fire to produce a sustained flame, which can be used to light charcoal, wood, or other types of fires. After the fire has burned out, the block can be re-used.

The block of the present invention can be used for a short period of time until the fire is started in the fuel to be burned, after which the block can be extinguished. If there is sufficient fuel left in the block, the block can be re-ignited. If the block is not extinguished before the fuel in the block is exhausted, the block can burn for about 20 minutes or more. After this, the block can be recharged with fuel for future use.

In a preferred embodiment of the present invention, the impregnated block is surrounded on the sides and bottom by a container of approximately the same size as the block. The container and block are placed in position to light combustible material. Once the fire is burned out, the container and block are removed for re-use.

Alternatively, the block can be used to release a fragrance or scent over an extended period of time. This is particularly useful to hunters who wish to camouflage their human scent when hunting wild animals. The block can also be impregnated with pleasant fragrances to release scents into an area such as a room over an extended period of time.

DETAILED DESCRIPTION OF THE INVENTION

Figure 1:
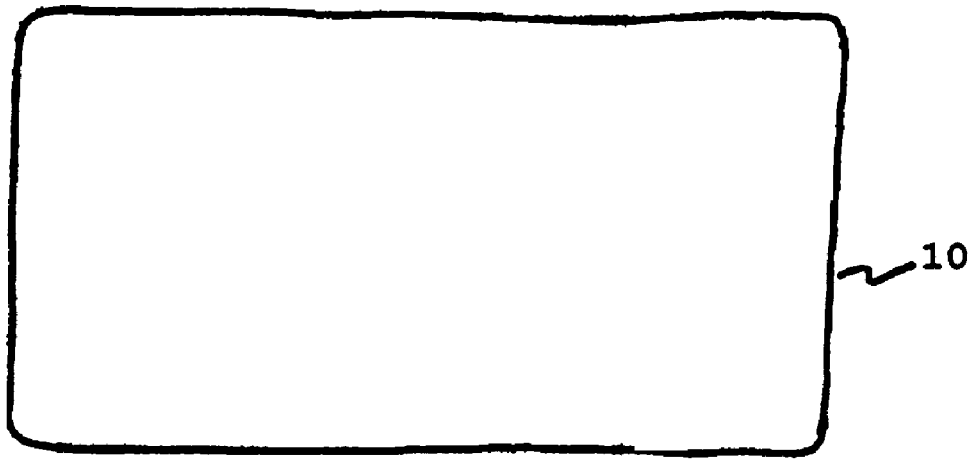
FIGS. 1A-C show one configuration of a calcium silicate block of the present invention in front plan view, side view, and end view.
Figure 1:
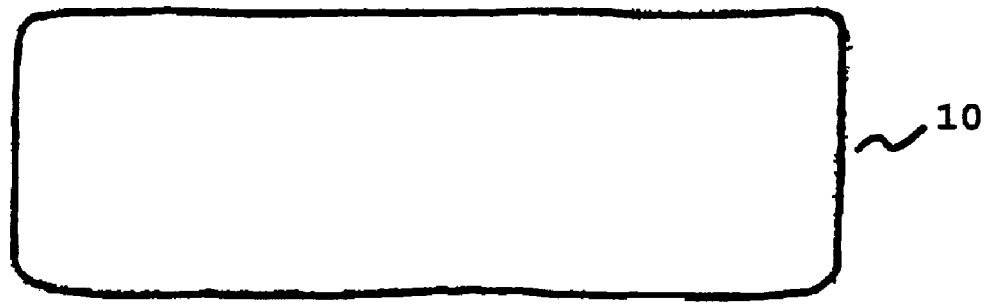
Figure 1:
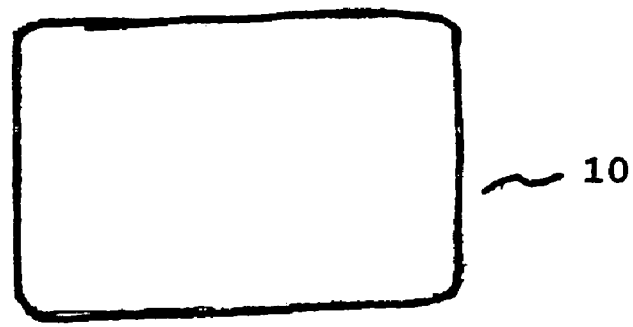

Calcium silicate hydrates possess a wide level of structural complexity. Over 30 crystalline phases are known, and for preparations near room temperature, there is an indefinite range of semi-crystalline to nearly amorphous phases of calcium silicate hydrates, all of which are described by the generic term, C—S—H.

Variations in solubility for stable C—S—H phases occur at Ca/Si ratios of about 1. It is believed that a given Ca/Si ratio can arise from more than one ionic constitution. C—S—H with a Ca/Si ratio of 0.8, for example, can increase its Ca/Si ratio through: omission of bridging silicate tetrahedral;
   a. increase in interlayer Ca balanced by loss of protons from Si—OH groups;
   b. increase in Ca balanced by OH, or
   c. various combinations of these effects.

The calcium silicate absorbents of the present invention have a xonotlite crystal structure that produces materials with extremely low water of hydration. This material can be readily machined into any size or shape to be used as an absorbent.

One example of a calcium silicate material that can be used in the present invention is SuperFiretempL®, a product of the Industrial Insulation Group, LLC. SuperFiretempL® has an average density of 18 pcf (288 kg/m2), an average flexural strength of 260 psi (1793 kPa), a compressive strength with 10% deformation of 450 psi (3103 kPa), and a moisture content of about 4% by weight.

Preferred methods for making a calcium silicate absorbent according to the present invention can be found in Kubo et al., U.S. Pat. No. 4,162,924, the entire contents of which are hereby incorporated by reference. A slurry of calcium silicate particles is formed, and then the slurry of calcium silicate particles is mixed with the other ingredients and shaped into the desired forms.

Typically, useful aqueous slurries of calcium silicate particles are prepared by mixing together milk of lime having a sedimentation value of at least 45 ml and predominantly crystalline silica in water in a water to solids ratio of at least 15:1 by weight. The slurry is subjected to hydrothermal reaction by heating the slurry under pressure to prepare a slurry of xonotlite crystals. The sedimentation volume refers to the volume of lime sedimented in a cylindrical container having a diameter of 1.3 cm and a capacity of at least 50 ml when 50 ml of milk of lime is placed into the container and allowed to stand for 20 minutes, the milk of lime having been prepared by hydration from water and lime in a water to solids ratio of 24:1 by weight. The large sedimentation volume indicates that the lime is stably well dispersed in water, thereby exhibiting high reactivity.

Milk of lime having a sedimentation volume of at least 45 ml can be prepared, for example, by vigorously agitating water and lime in a water to solids ratio of at least 5:1 by weight at a high speed, preferably at a temperature of at least 60° C. Various limes are suitable for preparing milk of lime, such as quick lime, slaked lime, carbide slag, and the like. Among these, quick lime is the most suitable for giving an increased sedimentation volume.

Useful siliceous materials for preparing the calcium silicate of the present invention are crystalline siliceous materials such as quartzite, quartz, sandstone quartzite, composite quartzite, silica sand, and the like. These siliceous materials generally have an average particle size of up to about 50 microns, preferably up to about 10 microns. Siliceous materials containing amorphous silica can also be used, as they consist predominantly of crystalline siliceous materials. It is also possible to use a mixture of crystalline siliceous material and less than about 50% by weight of amorphous silica.

The lime and siliceous materials are used in a ratio desirable for the formation of xonotlite crystals. The mole ratio of lime to siliceous material is preferably about 0.85 to about 1.1, and more preferably about 0.92 to 1.0 to form xontolite crystals. The lime milk and siliceous material are mixed together in a water to solids ratio of at least about 15:1 to obtain a starting slurry. The starting slurry is heated with agitation at increased pressure for hydrothermal reaction. The reaction conditions such as pressure, temperature, agitating speed, etc. are suitable determined in accordance with the reactor, agitator, and the type of crystals desired. The hydrothermal reaction is conducted usually at a temperature of at least about 175° C. and at a pressure of at least 8 kg/cm². The preferred reaction conditions are 191° C. and 12 kg/cm² for the production of xonotlite crystals. The reaction time can be reduced by elevating the temperature and pressure, and a shorter reaction time is economically advantageous. In view of safety considerations the preferred reaction time is about ten hours.

The agitation speed for the hydrothermal reaction is suitable determined in accordance with the kinds of materials and the reactor and the reaction conditions. For example, the agitating speed is about 100 rpm when a starting slurry having a water to solids ratio of 24:1 by weight and consisting of milk or lime with a sedimentation volume of 50 ml and finely divided siliceous material with an average particle size of about 5 microns is subjected to a hydrothermal reaction at 191° C. and 12 kg/cm2 in a three liter reactor having a diameter of 150 mm and equipped with paddle-shaped blades.

Agitation can be effected by rotating or vibrating the reactor itself or by forcing a gas or liquid into the reactor, or by some other method of agitation.

The hydrothermal reaction can be carried out batchwise or continuously. When the reaction is conducted in a continuous manner, the starting slurry is continuously forced into the reactor while the reacted slurry, the slurry of calcium silicate crystals, is withdrawn at atmospheric pressure. Alternatively, the staring slurry may be reacted at a reduced ratio of water to solids, such that the resulting slurry may be run off with a specified quantity of water forced into the reactor after the reaction.

To precipitate calcium silicate crystals, a reaction accelerator, catalyst, nonsettling agent and the like can be added to the starting slurry as desired. Examples of such additives include wollastonite, calcium silicate hydrate, alkali such as caustic soda, or caustic potash, and various salts of alkali metals.

To produce the aqueous slurry or globular secondary parties, the starting slurry prepared from lime milk and siliceous material, with addition of water when desired, can further incorporate asbestos fibers, ceramic fibers, rock wool, borosilicate glass, and bentonite clay. The resulting mixture is then subjected to hydrothermal reaction to produce an aqueous slurry in which the globular secondary particles of the invention and the inorganic fibers are uniformly dispersed in water. When dried, this aqueous slurry affords the globular secondary particles of the blocks used in the present invention. The globular secondary particles, since they are in the form of a shell composed of closely interlocked xontolite crystals, and having a hollow interior space, shaped bodies prepared therefrom have high mechanical strength with a very small apparent density.

More details regarding the preparation of blocks to be impregnated according to the present invention can be found in U.S. Pat. Nos. 4,162,924 and 4,298,386, to Kubo et al., the entire contents of which are hereby incorporated by reference.

The blocks of the present invention have excellent heat resistance, so that they can be used multiple times as fire starters.

To use the blocks as fire starters, a block of a size that fits comfortably on a barbecue grill or inside a fireplace is impregnated with at least one flammable material, such as candle wax (melted for impregnation), odorless mineral spirits, or propylene glycol, and mixtures thereof. The block can then be wrapped with an airtight material.

The calcium silicate block of the present invention can be of any desired shape or size, although a block shape rather than a cylindrical shape is preferred. FIGS. 1A-C illustrate a block that can be used according to the present invention. Figure A is a top plan view of the block 10. FIG. 1B is a side view of the block 100. FIG. 1C is a view of the block 100 standing on end.

In a preferred embodiment of the present invention, the block is contained within a holder that can be used in conjunction with the block to start fires. Preferably, the container has openings at the bottom to permit air to flow through the block and aid in maintaining the fire for a longer period of time than would be possible if the holder did not have openings in the bottom.

Figure 2:
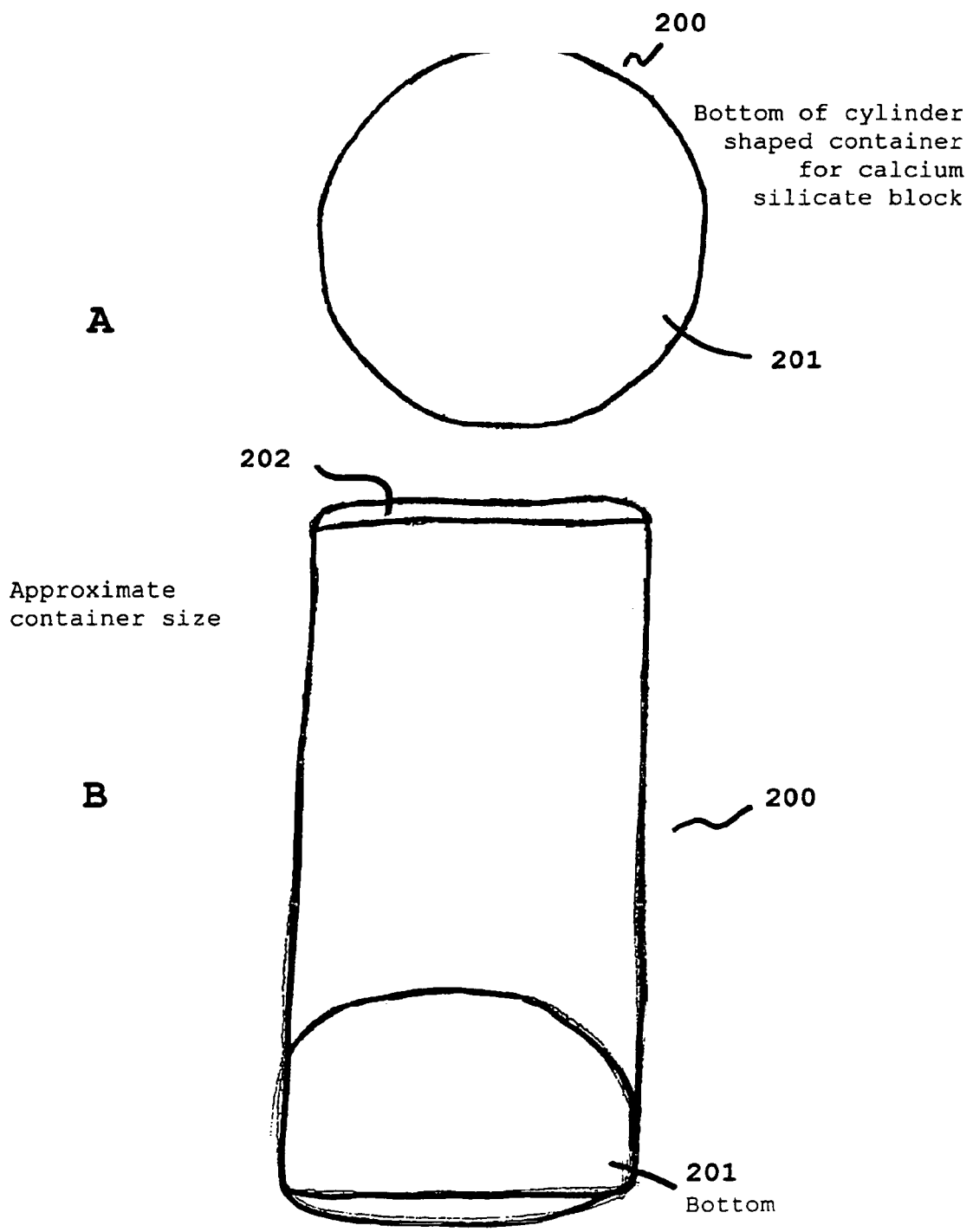
FIG. 2A shows the bottom of a cylindrical shaped container for a calcium silicate block.
FIG. 2B illustrates the cylindrical container for housing the calcium silicate block.

One type of container is illustrated in FIGS. 2A and 2B. FIG. 2A shows a bottom plan view of a cylindrical shaped container for the block. FIG. 2B shows an upright side view of the container 200 showing a top 202 which may be any type of readily removable top, such as a snap-on top, a screw-on top, and the like.

Once the combustible material, charcoal, briquettes, logs, etc., is arranged in place, the fire starter of the present invention is placed near the combustible material. Preferably, the impregnated block is placed under the combustible material so that flames originating from the block will rise upwardly towards the combustible material and ignite it. Once the fire has been extinguished, the block and holder can be removed and the block re-impregnated with lighter material to be used to start another fire.

In addition to the igniter, the block can be impregnated with a dye to make the block more colorful, or with salts that cause colored flames (nickel, sodium, potassium, copper, and the like).

For use in dispensing fragrances, the block is impregnated with the desired fragrance material and packaged so that the fragrance is maintained in the block. Once the packaging is opened, the block immediately begins releasing fragrance over a long period of time.

In one embodiment, the block is impregnated with a mixture of glycerol, ethanol, and 6-methylionone (fragrance of violets).

For use in hunting, the block is impregnated with deer urine or other animal fragrance that covers the smell of humans. When the hunters are in the woods, they maintain the block in their vicinity to cover up their human smell.

The blocks of the current invention can also be used for dispersing other volatile materials over and extended period of time. These materials include insecticides, insect repellants, animal repellents, disinfectants and the like.

The block of the present invention has been found to be unexpectedly superior to other commercially available calcium silicate blocks in fire starting. The control block was a block of 1050 Insulation Board manufactured by Insulite, Ltd. This block has the following chemical analysis: $SiO_2$ 44%, $TiO_2$ 0.1%, $Al_2O_3$ 0.5%, $Fe_2O_3$ 0.2%, MgO 1.5% CaO 42% $Na_2O$ 0.1%, $K_2O$ 0.1%, LOI (1050° C.) 10.5%. The dimensions of the control block were 1⅞ inch by 1³⁄₁₆ inch by 3¹³⁄₁₆ inches.

The block of the present invention had the dimensions 1¹⁵⁄₁₆ inch, 1³⁄₁₆ inch, and 3¾ inches.

Each block was introduced into an identical container, and an equal amount of charcoal lighter fluid was poured into each container. The times for absorption and shaking the block to distribute the fluid were identical. The blocks and fluid remained in their respective containers for 12-15 minutes. Three or four ounces of fluid was poured into each container for each individual burn test. The ounces for each test are shown in Table 1.

The units were place on their long narrow side in a fireplace. Once ignited, each unit burned until it was completely extinguished. The fireplace was vented and the units were placed directly below the vent, about 8-9 inches apart. The units were placed on alternate sides for each test, once on the right side of the firebox and then on the left side of the firebox, but still equally centered under the vent.

The test results are shown in Table 1

TABLE 1

| Amount of fluid | Control burn time | Present invention burn time |
| --- | --- | --- |
| 4 ounces | 20.15 min. | 23.00 min. |
| 3 ounces | 17.15 | 19.00 |
| 3 ounces | 16.15 | 16.30 |
| 3 ounces | 18.00 | 21.00 |
| 3 ounces | 18.00 | 19.30 |
| 3 ounces | 18.30 | 20.00 |
| 3 ounces | 17.15 | 18.45 |
| 3 ounces | 15.15 | 16.45 |
| 4 ounces | 17.30 | 20.00 |
| 4 ounces | 17.15 | 21.00 |
| 4 ounces | 17.45 | 21.15 |
| 4 ounces | 17.30 | 21.00 |

It is clear from the results shown in Table 1 that the block of the present invention is superior to a conventional calcium silicate block.

The foregoing description of the specific embodiments will so fully reveal the general nature of the invention that others can, by applying current knowledge, readily modify and/or adapt for various application such specific embodiments without undue experimentation and without departing from the generic concept. Therefore, such adaptations and modifications are and should intend to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

What is claimed is:

1. A sustained release composite comprising a three-dimensional piece of calcium silicate having a xonotlite structure and which includes fibers of textile glass and borosilicate glass, and a fire starting agent.

2. The composite according to claim 1 wherein the calcium silicate in addition to the fire starting agent, contains about 0.5% wood pulp fibers, from about 0.5% to about 1% textile grade glass fibers, and about 1% bentonite clay.

3. The composite according to claim 1 wherein the fire starting agent is selected from the group consisting of candle wax, mineral spirits, propyleneglycol and mixtures thereof.

4. The composite according to claim 1 wherein the composite is packaged in a package made of a material that maintains the fire starting agent in the composite until the package is opened.

5. The composite according to claim 4 wherein the package is a cylindrical container.

6. The composite according to claim 5 wherein the cylindrical container has a snap on top.

7. A method for forming a fire starter comprising impregnating a block comprising a three-dimensional piece of calcium silicate having a xonotlite structure and in which are fibers of textile glass and borosilicate glass with a fire starting material.

8. The method according to claim 7 wherein the calcium silicate, in addition to the fire starting agent, contains about 0.5% wood pulp fiber, from about 0.5% to about 1% textile grade glass fibers and about 1% bentonite clay.

* * * * *